United States Patent [19]

Ashmead

[11] 4,076,803
[45] Feb. 28, 1978

[54] SYNERGISTIC COMBINATION OF METAL PROTEINATES WITH BETA-CHLOROVINYL DIALKYL PHOSPHATES

[76] Inventor: Harvey H. Ashmead, 719 E. Center Street, Kaysville, Utah 84037

[21] Appl. No.: 666,868

[22] Filed: Mar. 15, 1976

[51] Int. Cl.² .................... A61K 37/00; A61K 31/66
[52] U.S. Cl. .................................. 424/177; 424/219
[58] Field of Search ............................. 424/219, 177

[56] References Cited

U.S. PATENT DOCUMENTS

| | | | |
|---|---|---|---|
| 3,160,556 | 12/1964 | Beaver et al. | 424/219 |
| 3,408,443 | 10/1968 | McAllister | 424/219 |
| 3,507,956 | 4/1970 | Batte et al. | 424/219 |

Primary Examiner—Sam Rosen
Attorney, Agent, or Firm—Criddle, Thorpe & Western

[57] ABSTRACT

Metals are transported throughout mammalian tissues and across the placental barrier to the foeti by the use of a synergistic mixture comprising an effective dosage of a metal proteinate and at least one beta-chlorovinyl dialkyl phosphate.

17 Claims, No Drawings

SYNERGISTIC COMBINATION OF METAL PROTEINATES WITH BETA-CHLOROVINYL DIALKYL PHOSPHATES

BACKGROUND OF THE INVENTION

This invention relates to synergistic compositions of metal proteinates with beta-chlorovinyl dialkyl phosphates. More particularly, this invention relates to the increase of metals throughout body tissues and increased passage across the placental barrier from the mother to the foeti when the mother is given a synergistic mixture comprising an effective dosage of a metal chelate and beta-chlorovinyl dialkyl phosphate, said phosphate preferably being a slow release form.

Beta-chlorovinyl dialkyl phosphates are well known in the art, as cholinesterase inhibitors, and are widely used and marketed as both pesticides and anthelminthics. Such compounds are most effectively administered in the form of slow release compositions which are particularly disclosed and claimed in U.S. Pat. No. 3,166,472 issued Jan. 19, 1965, U.S. Pat. No. 3,318,969 issued May 9, 1967, and U.S. Pat. No. 3,507,956 issued Apr. 21, 1970.

In U.S. Pat. No. 3,507,956 there is disclosed a method of increasing the vitality of the fetus of a mammal and a newborn animal which comprises administering to the pregnant female mammal an effective amount of a beta-chlorovinyl dialkyl phosphate. That patent purports to show an increase in the overall vitality of piglets that are born from sows which have been treated with 2,2-dichlorovinyl dimethyl phosphate (DDVP) which has been administered as a slow release formulation utilizing polyvinyl chloride as the embedding resin. The data purportedly show greater survivability, fewer incidents of stillborn piglets, and faster weight increase to market weight of piglets treated with the 2,2-dichlorovinyl dimethyl phosphate. Similar data is also shown for dogs. In the patent, the only substantial difference within the internal organs of the animal is that the blood glucose results are higher in animals that have been treated with the 2,2-dichlorovinyl dimethyl phosphate. Such is not the case in the present invention.

Commercial preparations of 2,2-dichlorovinyl dimethyl phosphate commonly known as DDVP or dichlorvos embedded in a plastic formulation for slow release purposes are presently being marketed by Shell Chemical Company under various trade names. For example, a swine anthelminthic is marketed under the trade name of ATGARD.®

In any growing mammal, swine in particular, it is extremely important that metals, iron in particular, be readily available to the growing fetus as well as to the newly born piglet.

It has been shown in copending application Ser. No. 658,243 filed Feb. 17, 1976, which is a continuation-in-part of Ser. No. 607,370 filed Aug. 25, 1975, now abandoned, which was in turn a continuation-in-part of Ser. No. 420,033, now abandoned, which was a continuation-in-part of Ser. No. 739,141 filed June 14, 1968, and now abandoned, that "metal proteinates", which are defined at page 89 of the *Official Publication of the American Feed Control Officials, Inc.* as "the product resulting from the chelation of a soluble salt with amino acids and/or partially hydrolyzed protein," increase the flow of metals across the placental wall as well as increasing the metals in tissues in mammals. The increased metal content is also present in the mammals milk after parturition.

It is known that metal proteinates require at least two ligands per mole of bivalent metal in order to form an intact chelate which forms a heterocyclic ring. Such chelates carry a zero net charge and are more readily absorbed in the small intestine and distributed throughout the body than are salts of proteins or inorganic metal salts.

OBJECTS OF THE INVENTION

It is an object of the present invention to provide a synergistic composition comprising a metal proteinate and a beta-chlorovinyl dialkyl phosphate to increase the metal content within body tissue and also increase the transfer of metal across the placental barrier of a mammal.

It is also an object of the present invention to provide novel synergistic composition of metal proteinates, iron proteinates in particular, with beta-chlorovinyl dialkyl phosphates which increase the metal in the tissues, increase the flow of metal across the placental barrier of the pregnant mammal and readily make the metal available in the milk of said mammal after farrowing or parturition.

Another object of this invention is to provide a method for the increased uptake of metals into the feoti of a pregnant mammal by administering to said mammal during the final stages of pregnancy an effective dosage of a synergistic mixture of a metal proteinate and a beta-chlorovinyl dialkyl phosphate.

A still furthr object of the present invention is to increase the uptake of metals into a baby mammal by administering to the mother a synergistic mixture of an effective dosage of a metal proteinate and a beta-chlorovinyl dialkyl phosphate whereby the young mammal obtains the synergistic mixture via the mother's milk.

These and other objects will become apparent by the following detailed description of the invention.

BRIEF SUMMARY OF THE INVENTION

It has been unexpectedly found that when effective dosages of metal proteinates, such as iron proteinate, are administered to mammals and to pregnant mammals in particular, with an effective amount of a beta-chlorovinyl dialkyl phosphate, a synergistic effect is obtained in increasing the metal content within the tissues and in transporting said metal throughout the body tissues and across the placental barrier into the unborn fetus.

The word synergism as applied here is a term which is applied to the usage of two biological preparations. The use of one, when utilized with the other, has a combined effect greater than the net effect of each when used separately.

In U.S. Pat. No. 3,507,956 it is thought that the unexpected results obtained by the use of beta-chlorovinyl dialkyl phosphates is that there appears to be an increased concentration of glucose in the blood of the fetus, as compared to control animals which have not been fed the phosphate material.

It is shown in Ser. No. 658,243, filed Feb. 17, 1976, and its parent applications, that amino acid proteinates, iron proteinate in particular, are superior in their ability to penetrate the placenta. This is due to the active transport of the intact proteinate (chelate) across the placental barrier.

Apparently, the action of the beta-chlorovinyl dialkyl phosphate is to dilate the small blood vessels and capillaries causing a greater blood flow to the placenta. Therefore, it is easier to transport components in the blood, whether it be blood glucose or chelated proteinates, across the placental barrier.

Regarding metal proteinates, it is thought that there might be a difference in the way different types of proteinates are metabolized. For example, a short-chained chelate such as a tri-glycine or a long-chained chelate such as tryptic digested casein would probably be transported and metabolized differently than a single amino acid chelate or a group of mixed amino acid chelates. Stated another way, the shorter the protein hydrolysate is the more readily it will be absorbed into the bloodstream and transported to the various tissues of the body.

While it has been found that metal proteinates, and iron proteinates in particular, are better utilized, this application should not be construed as being limited to any particular metal proteinate but includes proteinates of all essential bivalent metals such as iron, zinc, magnesium, manganese, copper, calcium, and cobalt. The ligand used to make the proteinate may be any hydrolysate from proteins including polypeptides, peptides, and naturally occurring amino acids and mixtures thereof. As previously stated, the metal proteinate or chelate forms a heterocyclic ring which is a coordination complex such that there is zero net electrical charge on the composition. Qualitatively, such proteinates are somewhat soluble in acidic solutions, but are insoluble precipitates in basic solutions. As previously stated, it is essential that each proteinate or chelate contain at least two ligands. The protein used may be hydrolyzed under either acidic or a basic condition or may be enzymatically digested by known methods. The chelate is formed by adding a soluble metal salt to a soluble protein hydrolysate under sufficiently basic conditions that the protons on the protein hydrolysates are removed thereby leaving the electrons on the hydrolysate, which would normally be attached to the protons, free to form coordinate complex bonds with the metal ions from the metal salt. The proteinate thus formed is precipitated and may be washed and then fed in desired dosages. Generally speaking, the amount of metal proteinate fed to mammals, whether pregnant or not will depend upon the percentage of metal in the proteinate. This, of course, will depend upon the particular metal being administered and can be determined on an empirical basis.

When administering an iron proteinate containing 10% by weight iron one will ordinarily mix from 3 to 12 pounds of iron proteinate to sufficient feed to make up 1 ton (2,000 pounds) of feed. Assuming the feed to be homogeneously mixed, each pound would therefore contain from about 0.0015 to 0.006 pounds of iron proteinate of which 10% would be iron. The dosage limits may vary considerably depending upon the size, sex, whether doing lactation and the general condition of the mammal.

For example, in a swine weighing 250 pounds and consuming 8 pounds of feed each day and using the above criteria, such swine would consume from 0.012 to 0.048 pounds of iron proteinate a day or 0.0012 to 0.0048 pounds of iron each day. Translated into milligrams of iron per pound of body weight per day, the amount would be from about 2 to 9 mg.lb. This range need not be construed as limiting but would probably constitute the preferred range for most metals fed to most mammals. The proteinate may be administered in divided dosages and will preferably be mixed with the food of the mammal such as the 3 to 12 pounds of proteinate per ton of feed as previously mentioned. Other levels of metal proteinates may be used in specialized cases. There has been no palatability problem when utilizing metal proteinates in this manner.

Numerous insecticidally active esters of phosphoric acids have been prepared as is illustrated by U.S. Pat. No. 2.956,073. A limited class of these pesticides have been shown to be useful in controlling endoparasites in both mammals and birds as well as being combined with resins to provide slow release pesticides. Such compositions are characteristically represented by the formula

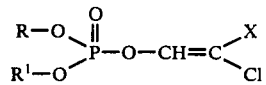

in which R and $R^1$ may be alkyl groups of from 1 to 4 carbon atoms and may be the same or different. X represents a member selected from the group consisting of hydrogen or chlorine. Typical of compounds of this class are 2-chlorovinyl phosphate; 2,2-dichlorodimethyl phosphate (DDVP); 2-chlorovinyl phosphate; 2,2-dichlorovinyl diethyl phosphate; 2,2-dichlorovinyl methyl ethyl phosphate; 2,2-dichlorovinyl methyl propyl phosphate; 2,2-dichlorovinyl methyl isopropyl phosphate; 2,2-dichlorovinyl methyl butyl phosphate; 2-chlorovinyl ethyl butyl phosphate.

The compounds of this class are generally known and the methods of preparation are taught in U.S. Pat. Nos. 2,956,073 and 3,299,190.

Preferably the chlorovinyl phosphates will be administered orally and may be conveniently mixed in the food of the animal. As with the proteinate, the phosphate can be administered in a single dose or in a series of doses over a specific period of time. Preferably, the chlorovinyl phosphate will be formulated in a slow release form rather than used as a neat composition.

Preparations which may be used for oral use may either by liquids or solids such as syrups, elixers, emulsions, powders, capsules or tablets. Such compositions are taught in U.S. Pat. No. 3,507,956.

As taught in the above mentioned patent, the phosphates will preferably be formulated in a polyvinylchloride resin for slow release. Such phosphates are readily soluble in such resins. The preparation of such a formulation may be made by warming and mixing the resin and phosphate together. Generally, the resin will contain from 10% to 30% by weight of the phosphate.

As previously stated, the phosphate can be administered to the mammal's food or may be combined with a carrier which is non-reactive with the phosphate, such as corn cob meal, walnut shell flour, citrus meal, bone meal, blood meal, fish meal and the like.

For continuous feeding for several days in the phosphate and proteinate may be mixed together in the mammal's feed and administered to the mammal at the same time. For single applications preferably the vinyl phosphte should be administered some 3 to 6 hours before the dose of metal proteinate is given. Presumably, as previously stated, the phosphate tends to dilate the bloof vessels. When administered to pregnant mammals, the vessels are diluted within the placental wall thereby enhancing the flow of blood across the placenta from the mother to the fetus.

The preferred phosphate is referred to as DDVP (2,2-dichlorovinyl dimethyl phosphate). Both the phosphate and the proteinate may be administered at any time. In the case of pregnancy, the synergistic mixture may be administered during the entire course of pregnancy and is advantageously administered during the latter portions of pregnancy. The period and dosage will depend upon the mammal and period of gestation. Normally the synergistic mixture should be given during the last trimester of pregnancy and from at least 1 week to 1 month prior to parturition.

While the data presented hereinafter relates primarily to laboratory animals, both the synergistic composition and the method of administering the same are applicable not only to laboratory animals such as mice, rats, ginuea pigs, rabbits, monkeys and the like, but also to pets such as dogs and cats and to fur bearing animals such as foxes, mink, and the like. The composition and method are also applicable to domestic animals such as swine, cattle, sheep, goats, horses, and the like, with emphasis being placed on swine. There is a particular problem with piglets in that they grow very rapidly and therefore require significant amounts of iron to avoid anemia. Oftentimes, this iron must be administered by injection to keep the piglet alive. It is believed that the present invention will solve this problem in that not only will the piglet be born with a higher hemoglobin content, but if the synergistic composition continues to be administered during lactation the young animal will continue with the increased uptake of metal achieved by means of the mother's milk.

In most mammals the dosage of the beta-chlorovinyl dialkyl phosphate varies from about 0.5 to 5 milligrams per pound of body weight per day with dosages of 2 to 3.5 milligrams per pound being preferred.

For pregnant swine the application of the synergistic mixture may begin, if not already in use, when the sow is placed in the farrowing house. The dosages previously stated may be administered. When using the phosphate in a slow release form it may be desirable to administer a higher dosage as only 20% to 50% of the phosphate may be released or made available during passage through the gastrointestinal tract depending upon the formulation.

The following examples are intended to be exemplary only and are not to be construed as limitations to the present invention.

EXAMPLE 1

In order to show the synergistic effect in increasing iron in tissues and in transporting iron across the placental wall utilizing 2,2-dichlorovinyl dimethyl phosphate along with the iron amino acid proteinate as a synergistic mixture, the following groups were set up.

Fifteen timed pregnant Sprague Dawley White Rats were fasted overnight and divided randomly into five groups and given the following dosages:

GROUP I

There was mixed together 75 ul (microliters) of distilled $H_2O$ and 4.4 uc (microcuries) of $Fe^{59}Cl_3$ dissolved in 10 ul of $H_2O$.

GROUP II

There was mixed together 75 ul of 2% triglycine buffered to a pH of 10 with a bicarbonate-carbonate buffer and 4.4 uc of $Fe^{59}Cl_3$ dissolved in 10 ul of $H_2O$ to form an iron triglycine chelate.

GROUP III

There was mixed together 71 ul of 2% tryptic peptide digest buffered to a pH of 10 with a bicarbonate-carbonate buffer and 4.4 uc of $Fe^{59}Cl_3$ dissolved in 10 ul of $H_2O$ to form an iron tryptic peptide digest chelate.

GROUP IV

There was mixed together 75 ul of 2% amino acid solution (hydrolyzed high vegetable protein plus methionine) buffered to a pH of 10 with a bicarbonate-carbonate buffer and 4.4 uc of $Fe^{59}Cl_3$ dissolved in 10 ul of $H_2O$ to form an iron amino acid chelate.

GROUP V

Same as GROUP IV except that 2 milligrams of 2,2-dichlorovinyl dimethyl phosphate in the form of a slow release polyvinyl chloride pellet (Shell AT-GARD®) was added.

In all occasions, except GROUP I, the buffered protein hydrolysate, whether it be a triglycine, tryptic peptide digest, or high vegetable protein-methionine mixture, immediately formed a chelate at the buffered basic pH.

All animals were dosed with the above dosages on a Friday afternoon and on the following Monday, one day before they were to give birth, the female rats were asphyxiated with ether and fetus and organs of the rats were removed and tested for $Fe^{59}$ radioactivity measured in corrected counts per minute (cc/min).

The fetus, along with the cord and placenta, were counted on a Nuclear-Chicago 2851 Gamma Counter with a 2 inch Sodium Iodide Crystal. The following results were attained:

| GROUP | NO. OF BABIES | CC/MIN × 100 COUNTS AVERAGE FETUS |
|---|---|---|
| I | 34 | 15.50 |
| II | 37 | 14.91 |
| III | 32 | 19.05 |
| IV | 32 | 18.07 |
| V | 36 | 45.98 |

The following tissues were dissected from the female rats and counted as above with the following cc/min × 100 counts:

| GROUP | UTERUS | LIVER | KIDNEY | SPLEEN | HEART | LUNG |
|---|---|---|---|---|---|---|
| I | 3,333 | 8,167 | 567 | 134 | 333 | 1,367 |
| II | 3,733 | 5,900 | 700 | 267 | 233 | 1,650 |
| III | 2,200 | 5,967 | 467 | 117 | 67 | 1,150 |
| IV | 4,925 | 9,675 | 950 | 325 | 1,425 | 2,925 |
| V | 14,333 | 39,133 | 2,433 | 1,433 | 5,033 | 10,834 |

As will be noted from the above data GROUP III which is the tryptic acid chelate and GROUP IV which is the amino acid chelate show about 25% better results in transporting iron across the placental wall than in GROUP I which is the control group. However, GROUP V, which is the amino acid chelate plus the 2,2-dichlorovinyl dimethyl phosphate synergistic mixture, was transported across the placental barrier about 300% better than GROUP I which is the control group.

In the tissues, GROUP V which is the synergistic mixture shows an increase in the radioactive iron content throughout the various organs of the female rat which is several hundred percent better than the control GROUP I and proteinate GROUPS II, III and IV made from a protein hydrolysate or amino acid.

In summary, the uptake of iron proteinates or chelates is markedly enhanced by the synergistic action of 2,2-dichlorovinyl dimethyl phosphate in the transport and absorption mechanisms throughout the various organs of the female rat and across the placenta wall into the fetus.

EXAMPLE II

In three separate experiments involving 36 timed pregnant 280 gram female rats and in excess of 340 young rats it has been demonstrated that mixtures of 2,2-dichlorovinyl dimethyl phosphate and iron amino acid chelates or proteinates are indeed synertistic. Experimental groups were set up in the following manner:

GROUP VI

Control Group

To this group was given 4 uc of $Fe^{59}Cl_3$ in 25 ul of $H_2O$ to which was added 50 ul of pH 10 buffer solution (bicarbonate-carbonate buffer). The rats were dosed orally with a 100 ul automatic pipette after being partially anesthetized with ether.

GROUP VII

$Fe^{59}Cl_3$ Plus 2,2-Dichlorovinyl Dimethyl Phosphate

To this group was given 4 uc of $Fe^{59}Cl_3$ in 25 ul of $H_2O$ to which was added 50 ul of a pH 10 buffer solution as used in GROUP VI. The rats were dosed orally with a 100 ul automatic pipette after they had been partially anesthetized with ether. Following the administration of the radioactive ferric chloride solution the rats were force fed with polyvinyl chloride pellets amounting to a dosage of 2 milligrams of 2,2-dichlorovinyl dimethyl phosphate (ATGARD ®) for each rat.

GROUP VIII

Iron Amino Acid Chelate

To this group was administered 4 uc of $Fe^{59}Cl_3$ in 25 ul of $H_2O$ which had been chelated with 50 ul of buffered amino acid solution. The solution added, therefore, was a buffered amino acid chelate. Each rat was dosed with 100 ul from an automatic pipette after the rats had been partially anesthetized with ether.

GROUP IX

Amino Acid Chelate Plus 2,2-Dichlorovinyl Dimethyl Phosphate

This group was the same as in GROUP VIII except the dosage of the amino acid was followed by the force feeding of 2 milligrams of 2,2-dichlorovinyl dimethyl phosphate in polyvinyl chloride (ATGARD ®) to each rat.

The dosages were given 3 days before the expected parturition date of the rats. Following are the results of the studies listed as an average and median plus or minus the standard deviation for the fetus. The whole body counts are given as corrected counts per minute or whole body counts (cc/min/rat):

| | |
|---|---|
| GROUP VI. | Control Group (4 uc $Fe^{59}Cl_3$). |
| | Average 18,160 ± 6,190 |
| | Median 17,800 ± 6,200 |

-continued

| | |
|---|---|
| GROUP VII. | $Fe^{59}Cl_3$ Plus 2,2-Dichlorovinyl Dimethyl Phosphate. |
| | Average 22,340 ± 5,670 |
| | Median 22,000 ± 5,680 |
| GROUP VIII. | Iron Amino Acid Chelate. |
| | Average 24,070 ± 11,400 |
| | Median 25,000 ± 11,400 |
| GROUP IX. | Iron Amino Acid Chelate Plus 2,2-Dichlorovinyl Dimethyl Phosphate |
| | Average 31,700 ± 16,600 |
| | Median 30,300 ± 16,700 |

As is obvious from the above results GROUP VII is higher up in uptake than is GROUP VI which is the control group. The 2,2-dichlorovinyl dimethyl phosphate appears to be beneficial in promoting the transport of iron across the placental barrier; however, the amino acid chelate in GROUP VIII is better than either the control GROUP VI or the 2,2-dichlorovinyl dimethyl phosphate GROUP VII in its ability to cross the placenta and enter the young rat. GROUP IX shows the synergistic action of the joint use of amino acid chelates and 2,2-dichlorovinyl dimethyl phosphate showing a 31% increase over GROUP VIII and a 42% increase over GROUP VII.

From the above, it is imminently obvious that by combining a metal proteinate (chelate) with a beta-chlorovinyl dialkyl phosphate that synergistic results are obtained in moving essential bivalent metals into tissues and across the placental wall. While the above results are directed to the utilization of iron as the essential metal and 2,2-dichlorovinyl dimethyl phosphate as the beta-chlorovinyl dialkyl phosphate they are considered to be exemplary only and the application is to be interpreted according to the scope of the appended claims.

What is claimed is:

1. A synergistic mixture for increasing the metal uptake of essential bivalent metals into the tissues of a mammal comprising an effective amount of a bivalent metal proteinate and a beta-chlorovinyl dialkyl phosphate of the formula

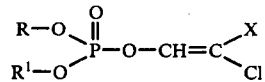

wherein R and $R^1$ are the same or different alkyl groups having from 1 to 4 carbon atoms and X is either hydrogen or chlorine.

2. A synergistic mixture according to claim 1 wherein R and $R^1$ each have one carbon atom and X is chlorine.

3. A synergistic mixture according to claim 2 wherein the bivalent metal is selected from the group consisting of iron, zinc, manganese, magnesium, calcium, copper and cobalt.

4. A synergistic mixture according to claim 3 wherein the metal proteinate and beta-chlorovinyl phosphate are combined in a feed mixture.

5. A synergistic mixture according to claim 4 wherein the metal proteinate is an iron proteinate.

6. A method for increasing the uptake of essential bivalent metals in a mammal which comprises administering to said mammal an effective synergistic dosage of a metal proteinate and a beta-chlorovinyl dialkyl phosphate of the formula

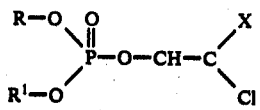

wherein R and R¹ are the same or different alkyl groups having from 1 to 4 carbon atoms and X is either hydrogen or chlorine.

7. A method according to claim 6 wherein R and R¹ each have one carbon atom and X is chlorine.

8. A method according to claim 7 wherein the bivalent metal is selected from the group consisting of iron, zinc, manganese, magnesium, calcium, copper and cobalt.

9. A method according to claim 8 wherein the iron proteinate is administered at the rate of 2 to 9 mg. per lb. of body weight per day and the beta-chlorovinyl phosphate is administered at the rate of 0.5 to 5 mg. per lb. of body weight per day.

10. A method according to claim 9 wherein the metal proteinate is an iron proteinate.

11. A method for increasing the transfer of essential bivalent metals across the placental wall of a pregnant mammal to a fetus which comprises administering to the pregnant mammal an effective synergistic dosage of a bivalent metal proteinate and a beta-chlorovinyl dialkyl phosphate of the formula

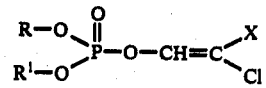

wherein R and R¹ are the same or different alkyl groups having from 1 to 4 carbon atoms and X is either hydrogen or chlorine.

12. A method according to claim 11 wherein R and R¹ each have one carbon atom and X is chlorine.

13. A method according to claim 12 wherein the metal proteinate is administered at the rate of from 2 to 9 mg. per lb. of body weight per day and the beta-chlorovinyl dialkyl phosphate is administered at the rate of 0.5 to 5 mg. per day.

14. A method according to claim 13 wherein the metal proteinate is an iron proteinate.

15. A method according to claim 14 wherein the mammal is a swine.

16. A method according to claim 13 wherein the synergistic mixture is administered in multiple dosages.

17. A method according to claim 16 wherein the beta-chlorovinyl dialkyl phosphate is administered separately and in advance of the iron proteinate.

* * * * *